(12) United States Patent
Nishiura

(10) Patent No.: US 12,249,417 B2
(45) Date of Patent: Mar. 11, 2025

(54) ULTRASONIC DIAGNOSTIC DEVICE AND DIAGNOSTIC ASSISTING METHOD

(71) Applicant: FUJIFILM Healthcare Corporation, Kashiwa (JP)

(72) Inventor: Tomofumi Nishiura, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 352 days.

(21) Appl. No.: 17/730,338

(22) Filed: Apr. 27, 2022

(65) Prior Publication Data

US 2022/0367038 A1    Nov. 17, 2022

(30) Foreign Application Priority Data

May 12, 2021 (JP) ................. 2021-080735

(51) Int. Cl.
*G06T 7/33* (2017.01)
*G06T 7/00* (2017.01)
*G16H 30/40* (2018.01)

(52) U.S. Cl.
CPC ........... *G16H 30/40* (2018.01); *G06T 7/0012* (2013.01); *G06T 7/33* (2017.01); *G06T 2207/10132* (2013.01); *G06T 2207/30096* (2013.01)

(58) Field of Classification Search
CPC ......... G16H 30/40; G06T 7/0012; G06T 7/33; G06T 7/73; G06T 2207/10132; G06T 2207/30096; G06T 2207/20084; G06T 2200/24; G06T 2207/20092; G06T 2207/20104; G06V 10/454; G06V 10/82; G06V 10/25; G06N 3/02; G06N 3/0464; G06N 3/04; G06N 20/00
See application file for complete search history.

(56) References Cited

U.S. PATENT DOCUMENTS

| | | | |
|---|---|---|---|
| 9,317,918 B2* | 4/2016 | Miyamoto | ............ G06T 7/0014 |
| 2013/0245426 A1 | 9/2013 | Lee et al. | |
| 2016/0022238 A1* | 1/2016 | Park | .................... A61B 6/5217 |
| | | | 600/407 |
| 2016/0171299 A1 | 6/2016 | Lee et al. | |

(Continued)

FOREIGN PATENT DOCUMENTS

| | | |
|---|---|---|
| JP | 2010-051553 A | 3/2010 |
| JP | 5982726 B2 | 8/2016 |

(Continued)

OTHER PUBLICATIONS

Jan. 9, 2024 Japanese official action (machine translation into English) in connection with Japanese Patent Application No. 2021-080735.

(Continued)

*Primary Examiner* — Gandhi Thirugnanam
*Assistant Examiner* — Michael Adam Shariff
(74) *Attorney, Agent, or Firm* — Paul Teng

(57) ABSTRACT

A detection unit detects a lesion candidate contained in display frame data (a tomographic image), using a machine learned detection model. An exclusion processing unit collates a feature vector of the detected lesion candidate with feature vectors registered in an exclusion database to determine whether the detected lesion candidate is an exclusion target. When the detected lesion candidate is an exclusion target, a mark display control unit restricts display of a mark for indicating a lesion candidate.

8 Claims, 9 Drawing Sheets

(56) References Cited

U.S. PATENT DOCUMENTS

2019/0295724 A1* 9/2019 Kanada ............... G16H 10/00
2021/0407082 A1* 12/2021 Smith ................. G16H 10/60
2023/0057933 A1 2/2023 Hayashida et al.

FOREIGN PATENT DOCUMENTS

| JP | 6297085 | B2 | 3/2018 |
| JP | 6710373 | B2 | 6/2020 |
| JP | 6815711 | B1 | 1/2021 |

OTHER PUBLICATIONS

Apr. 23, 2024 Japanese official action (machine translation into English) in connection with Japanese Patent Application No. 2021-080735.

* cited by examiner

ULTRASONIC DIAGNOSTIC DEVICE AND DIAGNOSTIC ASSISTING METHOD

CROSS REFERENCE TO RELATED APPLICATION

This application claims priority to Japanese Patent Application No. 2021-080735 filed on May 12, 2021, which is incorporated herein by reference in its entirety including the specification, claims, drawings, and abstract.

TECHNICAL FIELD

The present disclosure relates to an ultrasonic diagnostic device and a diagnostic assisting method, in particular, to a technique for notifying an examiner of a lesion candidate.

BACKGROUND

In an ultrasonic examination, a probe is placed on and scans along the surface of an examinee. During the scanning, real time tomographic images are displayed on a display and observed by an examiner to determine presence or absence of a lesion. If a lesion is found, the lesion portion is further examined in detail.

In the above, visual specification of a lesion portion, which temporarily appears in dynamically changing tomographic images, is not an easy task. To assist specification of lesion portions, Computer Aided Detection (CADe) is an available technique. Specifically, this technique detects a candidate for a lesion portion contained in a tomographic image, and notifies the examiner of the detected candidate for a lesion portion by, for example, showing a mark encircling the detected candidate for a lesion portion on the tomographic image. CADe is used together with or included in Computer Aided Diagnosis (CAD). Computer Aided Diagnosis may be denoted also as CADx.

The specification of JP5982726 discloses a data analysis system having a CAD function. The system includes an automatic detection device for executing calculation of feature vectors, comparison between feature vectors and learned data, and so forth. If a lesion candidate should be erroneously recognized, relearning is conducted. The above-mentioned JP5982726 does not disclose a technique for preventing erroneous recognition without relearning.

A lesion portion mentioned in the specification of this application refers to a portion that is possibly affected with a lesion or a portion in need of scrutinizing. A candidate for a lesion portion refers to a portion that is detected to assist specification of a lesion portion for diagnosis by an examiner.

An ultrasonic diagnostic device detects a candidate for a lesion portion, or a lesion candidate, using a machine learning detection unit, and displays a mark for notifying the examiner of the lesion candidate together with an ultrasonic image. In the ultrasonic diagnostic device, to correct a portion where to display a mark, or a marking target, generally, a machine learning detection unit is made to conduct relearning. Relearning, however, generally takes a considerable time to complete. As relearning is not readily conducted, a need for flexible correction of a marking target, depending on examinees, the purposes of examinations, medical institutes, or the like, is not currently satisfied.

An object of the present disclosure, therefore, is to enable flexible correction of a lesion candidate that is a marking target, in an ultrasonic diagnostic device for detecting a lesion candidate using a machine learning detection unit. Alternatively, the present disclosure aims to provide a new mechanism that can reduce the need for relearning by a machine learning detection unit.

SUMMARY

According to one aspect of the present disclosure, there is provided an ultrasonic diagnostic device including a detection unit having a machine learned detection model, the detection unit being for detecting a lesion candidate in an ultrasonic image; a database for containing features of lesion candidates to be excluded; a determination unit for collating a feature of the detected lesion candidate with the features registered in the database to thereby determine whether the detected lesion candidate is an exclusion target; and a display control unit for displaying a mark for indicating the detected lesion candidate on the ultrasonic image in the case where the detected lesion candidate is not an exclusion target, and for restricting display of the mark in the case where the detected lesion candidate is an exclusion target.

According to another aspect of the present disclosure, there is provided a diagnostic assisting method including the steps of detecting a lesion candidate in an ultrasonic image, using a machine learned detection model; registering features of lesion candidates to be excluded; collating a feature of the detected lesion candidate with the features registered in the database to thereby determine whether the detected lesion candidate is an exclusion target; and displaying a mark for indicating the detected lesion candidate on the ultrasonic image in the case where the detected lesion candidate is not an exclusion target, and restricting display of the mark in the case where the detected lesion candidate is an exclusion target.

According to another aspect of the present disclosure, there is provided a non-temporary storage medium storing a program for causing an information processing device to execute a diagnostic assisting method, the program for causing the information processing device to implement functions of detecting a lesion candidate in an ultrasonic image, using a machine learned detection model; registering features of lesion candidates to be excluded; collating a feature of the detected lesion candidate with the features registered in the database to thereby determine whether the detected lesion candidate is an exclusion target; and displaying a mark for indicating the detected lesion candidate on the ultrasonic image in the case where the detected lesion candidate is not an exclusion target, and restricting display of the mark in the case where the detected lesion candidate is an exclusion target.

BRIEF DESCRIPTION OF DRAWINGS

Embodiment(s) of the present disclosure will be described based on the following figures, wherein.

DESCRIPTION OF EMBODIMENTS

Figure 1:
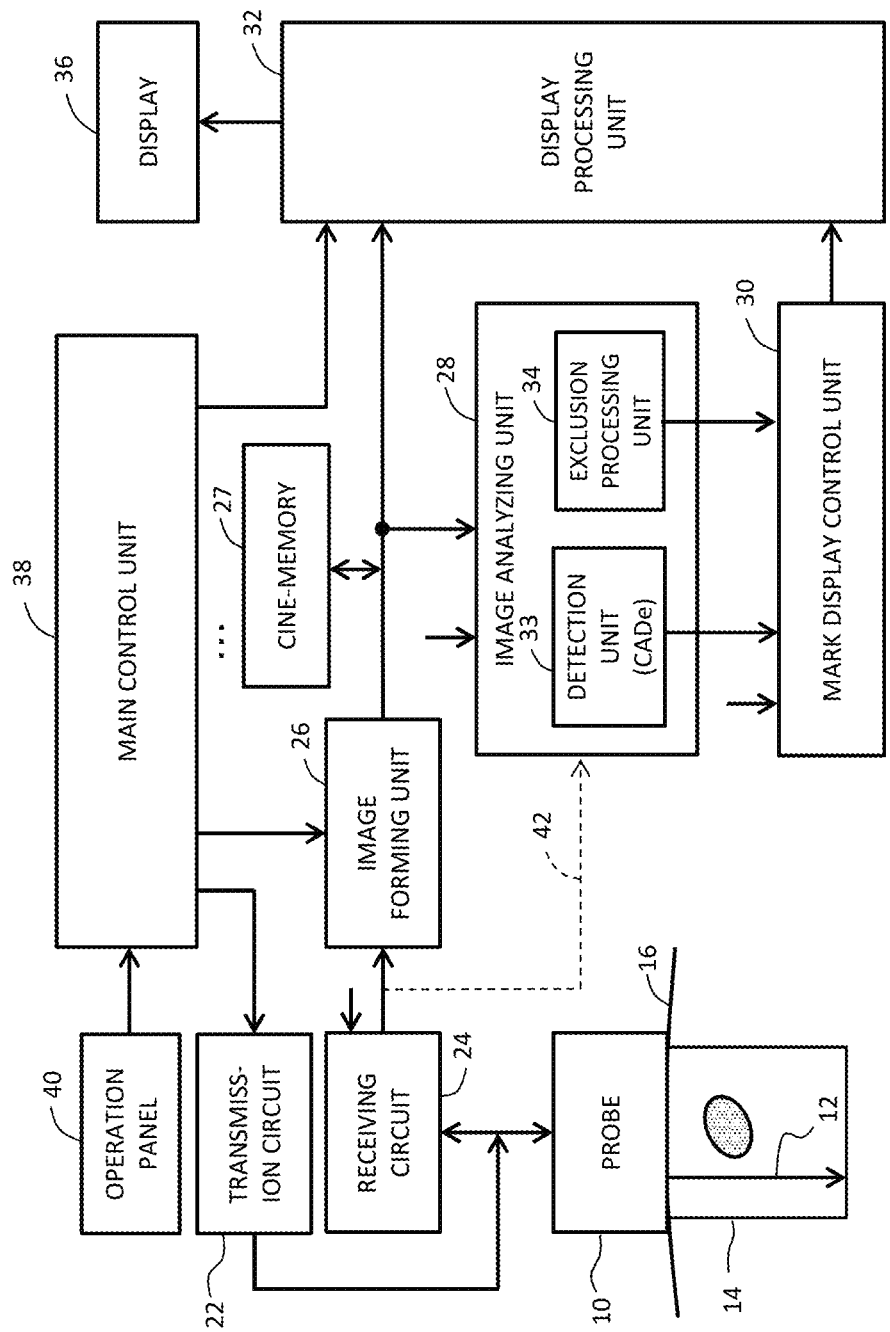
FIG. 1 is a block diagram illustrating the structure of an ultrasonic diagnostic device according to an embodiment.

Embodiments of the present disclosure will now be described by reference to the drawings.

(1) Outline of Embodiment

An ultrasonic diagnostic device according to an embodiment includes a detection unit, a database, a determination unit, and a display control unit. The detection unit has a machine learned detection model, and detects a candidate for a lesion portion, or a lesion candidate, in an ultrasonic image. The database contains features of lesion candidates to be excluded; that is, lesion candidates that are exclusion targets, registered therein for every lesion candidate to be excluded. The determination unit collates a feature of a detected lesion candidate with the features registered in the database, to thereby determine whether the detected lesion candidate is an exclusion target. If the detected lesion candidate is not an exclusion target, the display control unit displays a mark for notifying the examiner of, or indicating, the detected lesion candidate on the ultrasonic image. Meanwhile, if the detected lesion candidate is an exclusion target, the display control unit restricts display of the mark. Note that the detection unit corresponds to a detector; the determination unit corresponds to a determiner; and the display control unit corresponds to a controller.

The above-described structure excludes some of the detection targets from targets to be marked, or marking targets, through post hoc processing so that the detection targets are not determined as marking targets. In other words, the above-described structure can readily restrict marking targets without modification of the machine learned detection model. In addition, this structure can readily release the restriction.

Note that the concept of a feature of a lesion candidate includes a feature to be extracted from a lesion candidate, that to be extracted from an image portion containing a lesion candidate and an area around the lesion candidate, and that to be extracted from an ultrasonic image containing a lesion candidate. Also, the concept of a feature includes a feature vector, an image pattern, and so forth. A mark for indicating a lesion candidate is a display element for specifying a lesion candidate in an ultrasonic image.

An ultrasonic diagnostic device according to this embodiment further includes an input unit and a registration unit. The input unit receives an instruction for exclusion, or an exclusion instruction, sent from a user who is observing a lesion candidate in an ultrasonic image and sees a mark on the ultrasonic image. The registration unit registers a feature of a lesion candidate addressed by an exclusion instruction in the database. This structure enables correction by a user, of lesion candidates to be marked; that is, lesion candidates that are marking targets, without relearning of a machine learned detection model. Note that the input unit corresponds to an inputter, and the registration unit corresponds to a register.

In this embodiment, the input unit receives an exclusion instruction in a frozen state. The registration unit registers a feature of a lesion candidate addressed by the exclusion instruction in the database in the frozen state to thereby update the database. Note that the frozen state is a state in which transmission and reception is not carried out or in which a static image is kept displayed.

In this embodiment, the input unit receives an exclusion instruction in a real time operation state. In the real time operation state, the registration unit specifies one or more sets of displayed frame data, based on the time of reception of the exclusion instruction. In addition, the registration unit in the real time operation state extracts a feature of a lesion candidate from the one or more sets of specified frame data, and registers the extracted feature in the database to thereby update the database.

The above-described structure can update the database in the real time operation state. For example, this structure can restrict display of a mark when a lesion candidate is erroneously detected. A real time operation state is a state in which an ultrasonic image is displayed as a motion image and transmission and reception are being carried out. For example, a plurality of sets of frame data over a predetermined period of time in the past immediately preceding the time of reception of an exclusion designation as a referential point are specified, and a plurality of features or a representative feature are extracted.

In this embodiment, the detection unit has a function of obtaining a feature of a lesion candidate. Alternatively, a calculation unit may be provided separately from the detection unit to calculate the feature of a lesion candidate. Note that the calculation unit corresponds to a calculator.

The ultrasonic diagnostic device according to this embodiment includes a management unit for clearing the entirety or a part of the database. In this embodiment, the database includes a plurality of tables, in each of which at least one feature is registered. The management unit selects a table to clear from among the plurality of tables. For example, a table may be provided for every examinee, for every ultrasonic examination, or for every examiner, and a table having been used may be cleared at a predetermined time. The management unit corresponds to a manager.

A diagnostic assisting method according to this embodiment includes a detection step, a registration step, a determination step, and a display control step. In the detection step, a lesion candidate in an ultrasonic image is detected using a machine learned detection model. In the registration step, features of lesion candidates to be excluded is registered in the database. In the determination step, a feature of the detected lesion candidate is collated with the features registered in the database to thereby determine whether the detected lesion candidate is to be excluded, or is an exclusion target. In the display control step, a mark for indicating the detected lesion candidate is displayed on the ultrasonic image when the detected lesion candidate is not an exclusion target. Meanwhile, when the detected lesion candidate is an exclusion target, display of the mark is restricted.

The above-described diagnostic assisting method is implemented as a function of hardware or software. In the latter case, a program for executing the diagnostic assisting method is installed into an information processing device via a portable storage medium or a network. The concept of an information processing device includes ultrasonic diagnostic devices, image processing devices, computers, and so forth. The information processing device includes a non-temporary storage medium storing the above-described program.

(2) Details on Embodiment

FIG. 1 is a block diagram illustrating the structure of an ultrasonic diagnostic device according to this embodiment. The ultrasonic diagnostic device is a medical device to be installed in medical institutes, such as hospitals, and forms ultrasonic images based on a reception signal obtained from transmitted and received ultrasonic waves with respect to a living body (an examinee). Target organs of an ultrasonic examination include breasts, for example.

In a group medical checkup for breasts, it is necessary to specify lesion portions in a short period of time without failure. The ultrasonic diagnostic device according to this embodiment is equipped with Computer Aided Detection (CADe) for automatic detection of a lesion candidate (for example, a portion with low brightness that may be a tumor) contained in an ultrasonic image to assist specification of a lesion portion by an examiner, to be described later in detail.

A probe 10 functions as a means for transmitting and receiving ultrasonic waves. Specifically, the probe 10 is a portable transceiver, and is to be held and operated by a user, or an examiner (doctors, examination technicians, and so forth). In ultrasonic diagnosis of breasts, the probe 10 is placed such that its transducing surface (specifically, the surface of an acoustic lens) abuts on the surface of the chest of an examinee, so that tomographic images are displayed on a real time basis. While observing the tomographic images displayed on a real time basis, the user manually moves the probe 10 for scanning on the surface of the chest. When a lesion candidate is specified in a tomographic image, the position and posture of the probe 10 are slowly adjusted so that the tomographic image is carefully observed with the probe 10 at a fixed position and posture.

The probe 10 of the illustrated exemplary structure includes a transducer array composed of a plurality of one-dimensionally aligned transducers. The transducer array produces an ultrasonic beam (a transmission beam and a reception beam) 12. Electrical scanning with an ultrasonic beam 12 forms a scanning surface 14. The scanning surface 14 is a surface for observation; that is, a two dimensional (2D) data capturing area. Known examples of an electronic scanning method using an ultrasonic beam 12 include an electronic sector scanning method, an electronic linear scanning method, and so forth. Convex scanning with an ultrasonic beam 12 may be applied. The probe 10 may incorporate a 2D transducer array so that volume data from the inside of a living body can be obtained through 2D scanning with an ultrasonic beam.

A positioning system for obtaining the position information of the probe 10 may be provided. A positioning system is composed of, for example, a magnetic sensor and a magnetic field generator. In this case, the probe 10 (precisely speaking, the probe head of the probe 10) has a magnetic sensor. The magnetic sensor detects a magnetic field formed by the magnetic field generator to provide three-dimensional (3D) coordinate information. Based on the 3D coordinate information, the position and posture of the probe 10 can be specified.

A transmission circuit 22 functions as a transmission beam former. Specifically, in transmission, the transmission circuit 22 supplies a plurality of transmission signals in a parallel manner to the transducer array, which produces a transmission beam. Meanwhile, in reception, when the transmission waves is reflected on the inside of a living body and returns to reach the transducer array, the plurality of transducers output a plurality of reception signals in parallel. A receiving circuit 24 functions as a reception beam former, and generates beam data through phase-alignment and summing (also known as delay and summing) with a plurality of reception signals.

For every electronic scanning, a plurality of sets of beam data aligned in the direction of the electronic scanning are formed, which constitute received frame data corresponding to the scanning surface 14. Each set of beam data is composed of a plurality of sets of echo data aligned in the depth direction. Downstream the receiving circuit 24, a beam data processing unit, not illustrated, is provided.

An image forming unit 26 is an electronic circuit for forming a tomographic image (a B-mode tomographic image), based on the received frame data. The image forming unit 26 has a digital scan converter (DSC). The DSC has a coordinate conversion function, a pixel interpolation function, a frame rate conversion function, and so forth. In further detail, the image forming unit 26 forms a display frame data array, based on the received frame data array. Each set of display frame data constituting the display frame data array is tomographic image data. A plurality of sets of tomographic image data constitute a real time motion image. Note that ultrasonic images other than tomographic images may be formed. For example, a color flow mapping image may be formed. A 3D image representing tissues in a 3D manner may be formed. In the illustrated exemplary structure, the display frame data array is sent to a display processing unit 32 and an image analyzing unit 28.

The image analyzing unit 28 is a module for implementing a CADe function. The image analyzing unit 28 has a detection unit 33 and an exclusion processing unit 34.

The detection unit 33 detects a lesion candidate for every set of display frame data; that is, for every tomographic image. The detection unit 33 includes a machine learning detection unit having a machine learned detection model. The detection unit 33 is composed of, for example, a convolutional neural network (CNN) or the like, and detects a closed area with low brightness as a candidate for a lesion portion (hereinafter referred to as a lesion candidate). Prior to detection of a lesion candidate by the detection unit 33, binary processing, noise removal, or the like may be applied to a tomographic image. The detection unit 33 outputs lesion candidate information after detection of a lesion candidate.

Lesion candidate information includes the position information of a lesion candidate, the size information of a lesion candidate, and credibility information on a detection, or the like. When credibility of a level higher than a predetermined level is obtained, detection of a lesion candidate is determined. The detection unit 33 has a function of calculating a feature vector as the feature of a lesion candidate.

The position information of a lesion candidate is, for example, coordinate information indicating the central point of the lesion candidate itself. Alternatively, the position information is coordinate information indicating the central point of a figure encircling a lesion candidate so as to be in contact with the lesion candidate. Note that the central point is a representative point. Alternatively, the central point can be a geometrical central point or the barycentric point of the figure. The size information of a lesion candidate is, for example, information indicating the size of the lesion candidate itself or that of a figure encircling the lesion candidate while being in contact with the lesion candidate. For example, the size of a lesion candidate can be specified based on the coordinates of the central point of the figure and those of the upper left corner of the figure. Providing that the coordinates of the central point are specified, the coordinates of the upper left corner of the figure may be considered the size information of the lesion candidate. Alternatively, the area of a lesion candidate may be obtained as the size information of the lesion candidate. A plurality of lesion candidates may be detected in parallel.

A feature vector is composed of a plurality of vector elements. For calculation of feature vectors, one or more publicly known feature vector calculation methods can be employed. For example, a multivariate analysis may be employed as a feature vector calculation method. An image pattern may be used as a feature. Examples of the feature of a lesion candidate include a feature to be extracted from the lesion candidate, that to be extracted from an image portion containing the lesion candidate and an area around the lesion candidate, and that to be extracted from an ultrasonic image containing the lesion candidate.

The exclusion processing unit 34 has an exclusion database. The exclusion processing unit 34 collates the feature vector of a lesion candidate presently detected by the detection unit 33 (a present lesion candidate) with the feature vectors contained in the exclusion database. In the case where a feature vector having a similarity of a level higher than a predetermined level is found; in other words, in the case where the detected lesion candidate is an exclusion target, the exclusion processing unit 34 outputs an exclusion instruction signal to a mark display control unit 30. Meanwhile, in the case where a feature vector having a similarity of a level higher than the predetermined level is not found; in other words, in the case where the detected lesion candidate is not an exclusion target, no exclusion instruction signal is outputted.

The mark display control unit 30 displays, or superimposes, a mark for indicating a detected lesion candidate on an ultrasonic image. The mark display control unit 30, however, does not display a mark in the case where the exclusion processing unit 34 outputs an exclusion instruction signal. As described above, a marking target is discriminated from a detection target, which enables post hoc customization for marking targets. In customization, relearning by the machine learned detection unit in the detection unit 33 is unnecessary. Graphic data containing a mark generated by the mark display control unit 30 are outputted to the display processing unit 32.

In displaying marks, the marks may be displayed in different manners to thereby express difference in degree of credibility of the detection. For example, for low credibility, the mark may be displayed in a cold color, and for high credibility, in a warm color. Alternatively, for low credibility, the mark may be displayed with lower brightness, and for high credibility, with higher brightness. Alternatively, for low credibility, the mark may be displayed with high transparency, and for high credibility, with low transparency. Alternatively, for low credibility, the mark may be displayed in a thin line, and for high credibility, in a thick line. Alternatively, for low credibility, the mark may be displayed in a broken line, and for high credibility, in a solid line. Alternatively, marks of different types may be switched with one another for displaying. For example, display of a rectangular figure may be switched with display of four display elements indicative of four respective corners of the rectangular figure. Two or more manners for displaying may be applied simultaneously.

The image forming unit 26, the image analyzing unit 28, and the mark display control unit 30 each include a processor. Alternatively, a single processor may function as the image forming unit 26, the image analyzing unit 28, and the mark display control unit 30. A central processing unit (CPU) to be described later may function as the image forming unit 26, the image analyzing unit 28, and the mark display control unit 30.

The display processing unit 32 has a color operation function, an image combining function, and so forth. The display processing unit 32 is supplied with an output from the image forming unit 26 and an output from the mark display control unit 30. Note that a mark encircling a lesion candidate is one element constituting a graphic image. Although in the present embodiment the mark display control unit 30 generates a mark, a main control unit 38, the display processing unit 32, or the like may generate a mark.

A display 36 includes a liquid crystal display (LCD), an organic electro-luminescent (EL) display, or the like. The display 36 shows a tomographic image as a motion image on a real time basis, and also a mark as a part of a graphic image. The display processing unit 32 includes a processor, for example.

The main control unit 38 controls the operations of the respective structural components illustrated in FIG. 1. The main control unit 38 includes a central processing unit (CPU) for executing a program in this embodiment. The main control unit 38 is connected to an operation panel 40. The operation panel 40 is an input unit; that is, an input device, and has a plurality of switches, a plurality of buttons, a trackball, a keyboard, or the like. A condition for displaying a mark, or a mark display condition, can be set or changed with the operation panel 40. The operation panel 40 is operated to register an exclusion target in the exclusion database.

Although in the present embodiment a display frame data array is inputted to the image analyzing unit 28, a received frame data array may be inputted to the image analyzing unit 28 (refer to reference numeral 42). In this case, another image forming unit may be provided separately from the image forming unit 26 to readily and promptly form images.

A cine-memory 27 has a ring buffer structure. The cine-memory 27 temporarily stores display frame data arrays within a predetermined period of time in the past immediately preceding the present time. In a frozen state to be described later, display frame data selectively read from the cine-memory 27 is displayed on the display 36 as a tomographic image (a static image). During display, the image analyzing unit 28 and the mark display control unit 30 may be operated again to register an exclusion target. Data generated in the image analyzing unit 28 and the mark display control unit 30 may be temporarily stored in a buffer, so that registration of an exclusion target can be performed using data read from the buffer.

Figure 2:
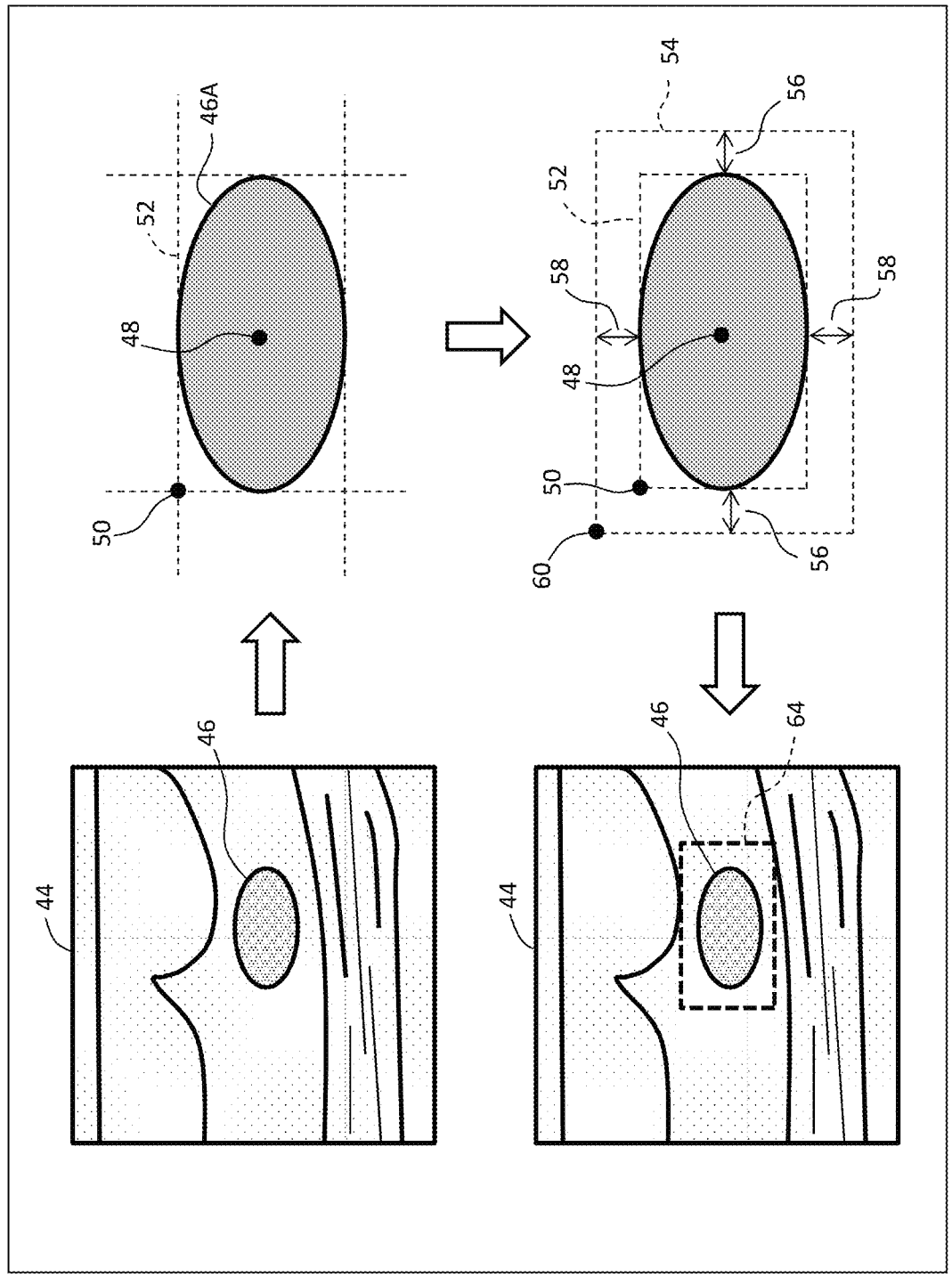
FIG. 2 is a diagram explaining a mark generation method.

FIG. 2 illustrates a mark generation method. A tomographic image 44 contains a lesion candidate 46. The tomographic image 44 is binarized to generate a binary image. Edge detection or area detection is applied to the binary image to extract a binarized lesion candidate 46A. For example, the coordinates of both ends of the lesion candidate 46A in the horizontal direction and those in the vertical direction together define a rectangle 52 that is circumscribed about the lesion candidate 46A. In actuality, the coordinates of the central point 48 of the rectangle 52 and those of the upper left corner 50 of the rectangle 52 are specified.

Further, another rectangle 54 is defined outside the rectangle 52 with predetermined margins 56, 58 in the horizontal and vertical directions, respectively. Specifically, the rectangle 54 is displayed as a mark 64 on the tomographic image 44. The mark 64 is a figure encircling the lesion candidate 46 and an area around the lesion candidate 46. In the illustrated example, the mark 64 is drawn in a broken line. Alternatively, a mark composed of four elements representing four respective corners of a rectangle may be displayed. Alternatively, a round or oval mark may be displayed.

In this embodiment, detection of a lesion candidate 46 is conducted in units of display frame data. In the case where a lesion candidate 46 is detected and the detected lesion candidate 46 is not an exclusion target, a mark 64 is displayed on the tomographic image 44 containing the lesion candidate 46. Displaying the mark 64 enables an examiner to be aware of the presence of a lesion candidate 46. This can prevent overlooking of a lesion candidate 46. Meanwhile, in the case where the detected lesion candidate 46 is an exclusion target, no mark 64 is displayed.

Figure 3:
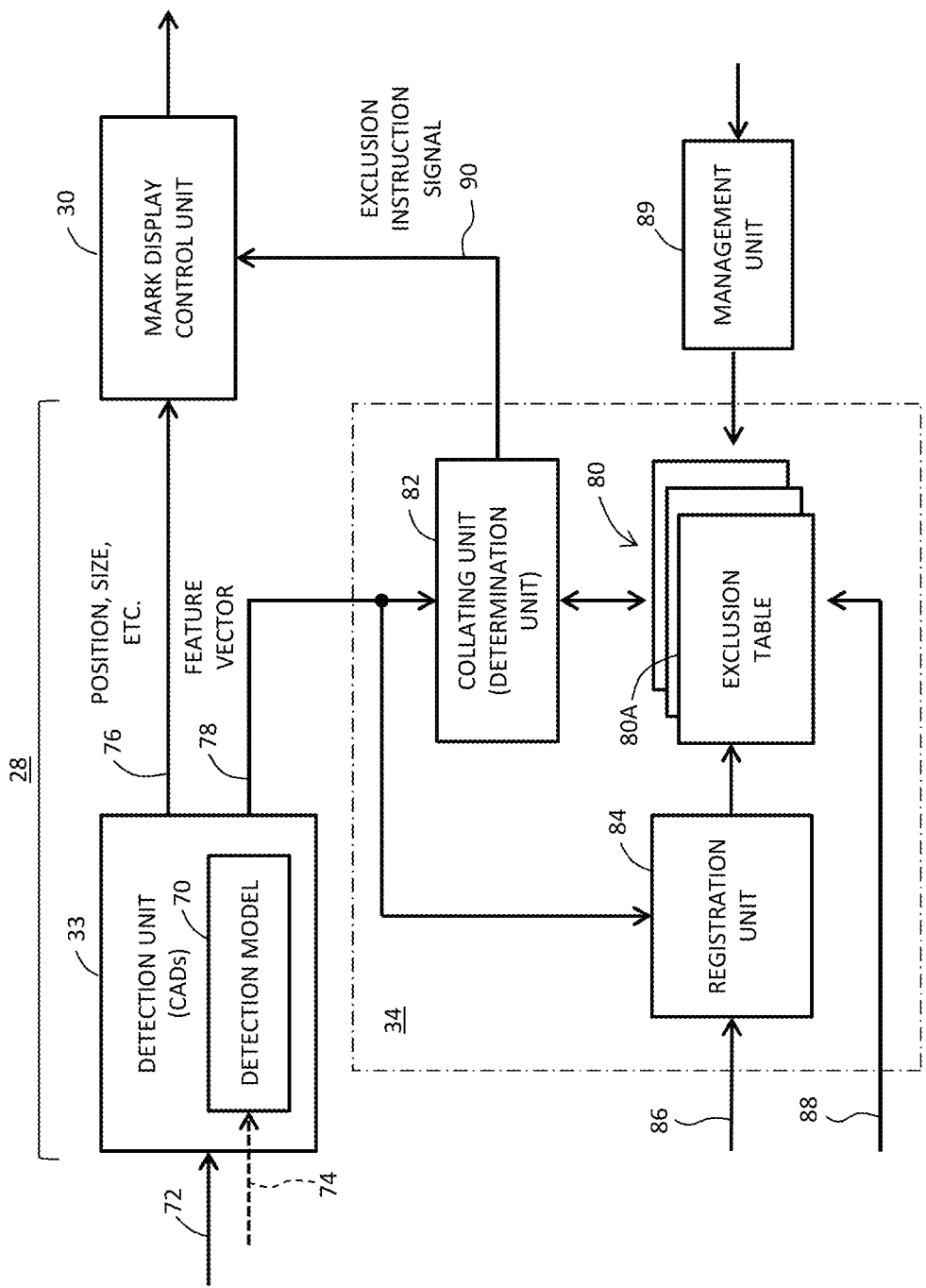
FIG. 3 illustrates a first exemplary structure of an image analyzing unit.

FIG. 3 illustrates a first exemplary structure of the image analyzing unit 28 illustrated in FIG. 1. The detection unit 33 has a machine learned detection model 70. Using the detection model 70, a lesion candidate contained in a tomographic image (display frame data) 72 is detected. The detection model 70 may contain a CNN parameter set, for example. Note that installation of a CNN parameter set is indicated with reference numeral 74. In this embodiment, the exclusion processing unit 34 is provided to enable correction of a marking target without relearning of the machine learned detection model 70. Position information, size information, and so forth, which constitute the lesion portion information, are inputted to the mark display control unit 30, as indicated with reference numeral 76.

The detection unit 33 has a function of calculating the feature vector of a lesion candidate. Information indicating a feature vector is sent to the exclusion processing unit 34, as indicated with reference numeral 78. Alternatively, a module different from the detection unit 33 may be provided to calculate a feature vector, to be described later with reference to FIG. 8.

The exclusion processing unit 34 includes an exclusion database 80, a collating unit (a determination unit) 82, and a registration unit 84. A management unit 89, to be described later, may constitute a part of the exclusion processing unit 34. In the illustrated exemplary structure, the exclusion database 80 is composed of a plurality of exclusion tables 80A. In actuality, an exclusion table 80A selected in response to a selection signal 88 is used. Needless to say, the exclusion database 80 may be composed of a single exclusion table. A plurality of exclusion tables 80A corresponding to a plurality of respective examinees may be provided; a plurality of exclusion tables 80A corresponding to a plurality of respective examiners may be provided; or a plurality of exclusion tables 80A corresponding to a plurality of respective medical specialties may be provided.

The collating unit 82 collates the feature vector of the presently detected lesion candidate with the feature vectors registered in the selected exclusion table 80A. Specifically, in the case where collation finds a feature vector of the present lesion candidate having a similarity of a level higher than a predetermined level, the present lesion candidate is determined as an exclusion target, and the collating unit 82 outputs an exclusion instruction signal 90 to the mark display control unit 30. Meanwhile, in the case that there is no feature vector having a similarity of a level higher than the predetermined level, no exclusion instruction signal 90 is outputted. As described above, the present lesion candidate can be evaluated post hoc in this embodiment. In other words, such a post hoc evaluation can eliminate the need for relearning of the detection model 70.

The registration unit 84 registers the feature vector of the present lesion candidate in the selected exclusion table. Registration of a feature vector can be performed in either the frozen state or the real time operation state, to be described later. Reference numeral 86 indicates a signal indicating a registration instruction issued by a user.

The management unit 89 clears the entirety or a part of the exclusion database 80. Specifically, the content of the exclusion table 80A can be cleared for every exclusion table 80A. For example, one or more exclusion tables 80A may be cleared in response to a clear instruction sent from a user. Alternatively, one or more exclusion tables 80A may be automatically cleared once a predetermined clearing condition is satisfied. For example, automatic clearing may be applied, for example, upon start of examination of a new examinee, upon change in a transmission/reception condition, or the like.

The mark display control unit 30 has a mark generation function and a mark display restriction function (generally, a function of not displaying a mark). The mark display control unit 30 generates a mark in the form of a figure encircling a lesion candidate, based on the lesion candidate information outputted from the detection unit 33. A mark may be displayed in a different manner, depending on credibility. Upon receipt of an exclusion instruction signal, the mark display control unit 30 does not generate a mark and does not display a mark. A mark is generated in units of a frame, and is determined to be displayed or not in units of a frame.

Figure 4:
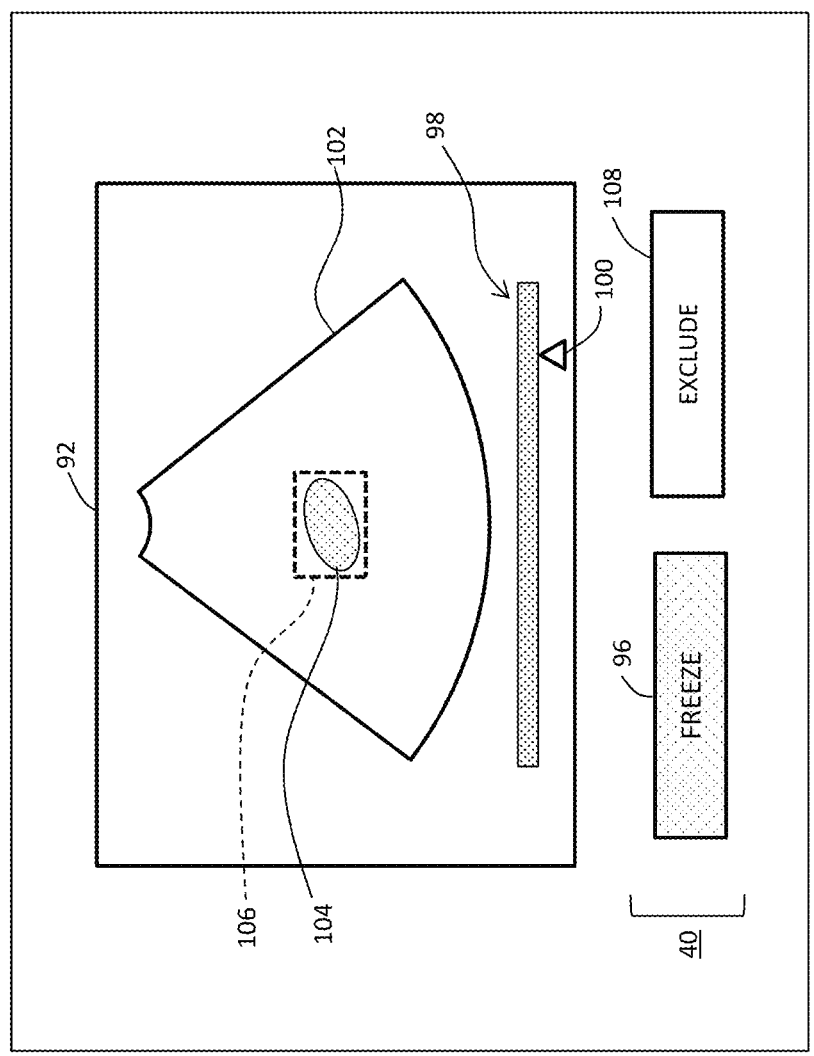
FIG. 4 schematically illustrates a first exemplary operation.

FIG. 4 schematically illustrates a first exemplary operation to be executed in a frozen state. A tomographic image 102 is displayed as a static image on a screen 92. That is, a freeze button 96 in the operation panel 40 has already been operated and a frozen state, in which transmission/reception is suspended, as described above, has been thereby set. In addition, a band figure is shown below the tomographic image 102, representing the storage area of the cine-memory. The right end of the band corresponds to the time at which a frozen state is set. Shifting a cursor 100 farther leftward along the band enables selection of display frame data in a farther past. Selected display frame data are displayed as the tomographic image 102. In the illustrated example, the tomographic image 102 contains a lesion candidate 104, with a mark 106 displayed encircling the lesion candidate 104.

If the mark 106 is displayed due to erroneous detection of a lesion candidate or if marking of the detected lesion candidate is not desired, an exclusion button 108 is operated. Then, the feature vector of the displayed lesion candidate is registered in the exclusion database (specifically, in the selected exclusion table), whereby the exclusion database is updated. Registration of exclusion targets is repetitively applied in the frozen state, when necessary. Re-operating the freeze button 96 releases the frozen state, with the real time operation state restored. In the real time operation state, whether a lesion candidate is an exclusion target is determined, based on the updated database.

Figure 5:
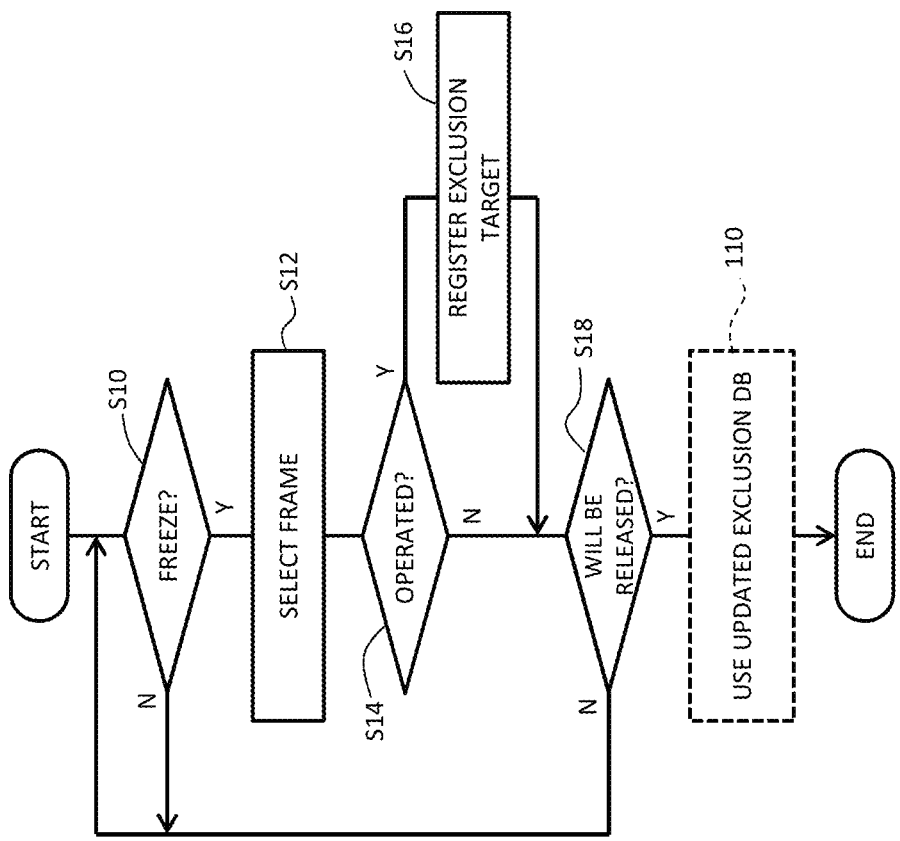
FIG. 5 is a flowchart of the first exemplary operation.

FIG. 5 is a flowchart of the first exemplary operation. In S10, a determination is made as to whether the freeze button has been operated, upon which the ultrasonic diagnostic device is put in the frozen state. In S12, a user performs a back-search with respect to the cine-memory to select specific display frame data. In S14, a determination is made as to whether an operation for instructing registration has been executed. Upon determination that an operation for registration has been executed, in S16 the feature vector of the displayed lesion candidate is registered in the exclusion database. That is, the exclusion database is updated. Thereafter, a series of processes in S10 and thereafter is repetitively executed until a determination is made in S18 that an operation for releasing the frozen state has been executed. After determination in S18 that an operation for releasing the frozen state has been executed, determination for a lesion candidate will be thereafter executed based on the updated exclusion database, as indicated with reference numeral 110.

Figure 6:
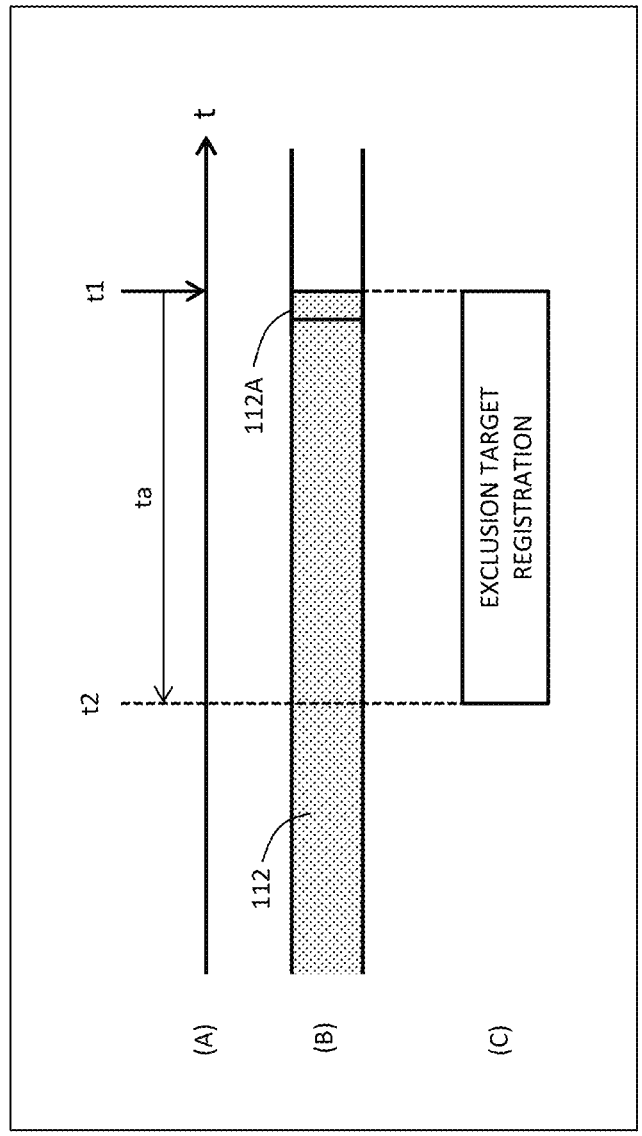
FIG. 6 schematically illustrates a second exemplary operation.

FIG. 6 schematically illustrates a second exemplary operation to be executed in the real time operation state, in which (A) corresponds to a timeline, with t1 indicating a time (the present time) when an exclusion operation is executed, and (B) corresponds to a cine-memory, where a display data array 112 is stored. Reference numeral 112A indicates the leading display frame data; that is, the latest display frame data stored in the cine-memory. In the second exemplary operation, an exclusion operation initiates registration of exclusion targets over a predetermined period of time ta in the past immediately preceding time t1, as indicated with (C). Note that the predetermined period of time ta may be, for example, N seconds, wherein N is one, two, three, and so forth, for example.

A determination is made as to whether a lesion candidate has been detected in each of the sets of display frame data in the predetermined period of time ta. Upon determination that a lesion candidate has been detected, the feature vector of the detected lesion candidate is automatically registered in the exclusion database. Specifically, a single feature vector may be calculated based on a plurality of lesion portions contained in a plurality of sets of respective display frame data, and registered in the database, the single feature vector representing the plurality of lesion portions. For example, in the case where a seemingly erroneous detection is performed in an ultrasonic examination, an examiner applies an exclusion operation (for example, by pressing an exclusion button). Then, a feature vector is registered in the database even in the real time operation state, whereby the database is updated. Thereafter, mark display control is executed based on the updated database.

Figure 7:
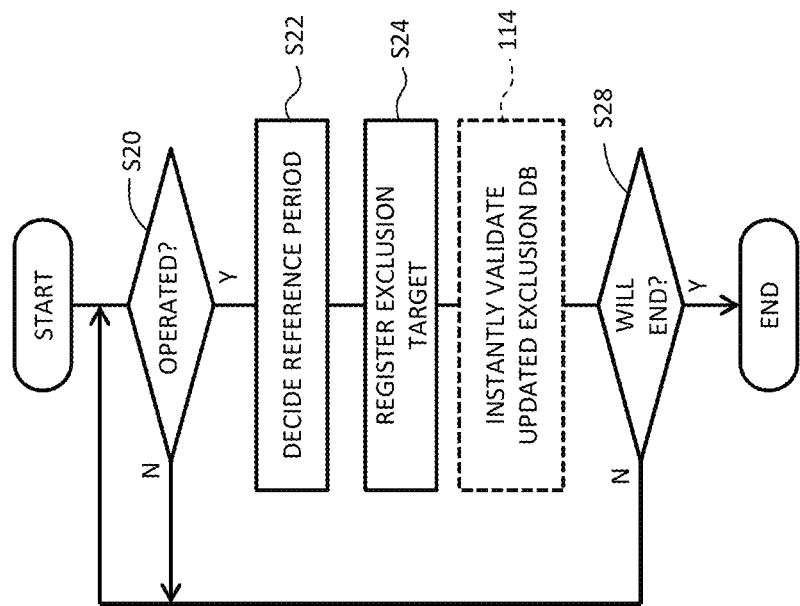
FIG. 7 is a flowchart of the second exemplary operation.

FIG. 7 is a flowchart of the second exemplary operation. In S20, a determination is made as to whether an exclusion operation has been performed. Upon determination that an exclusion operation has been performed, a reference period is decided in S22, and respective sets of display frame data within the decided reference period are checked in S24. In the case where any lesion candidate is contained in the display frame data, the feature vector of the contained lesion candidate is registered in the exclusion database, whereby the exclusion database is sequentially updated. That is, the updated exclusion database is instantly validated for use, as being indicated with reference numeral 114. In S28, a determination is made is as to whether to end the registration processing.

Figure 8:
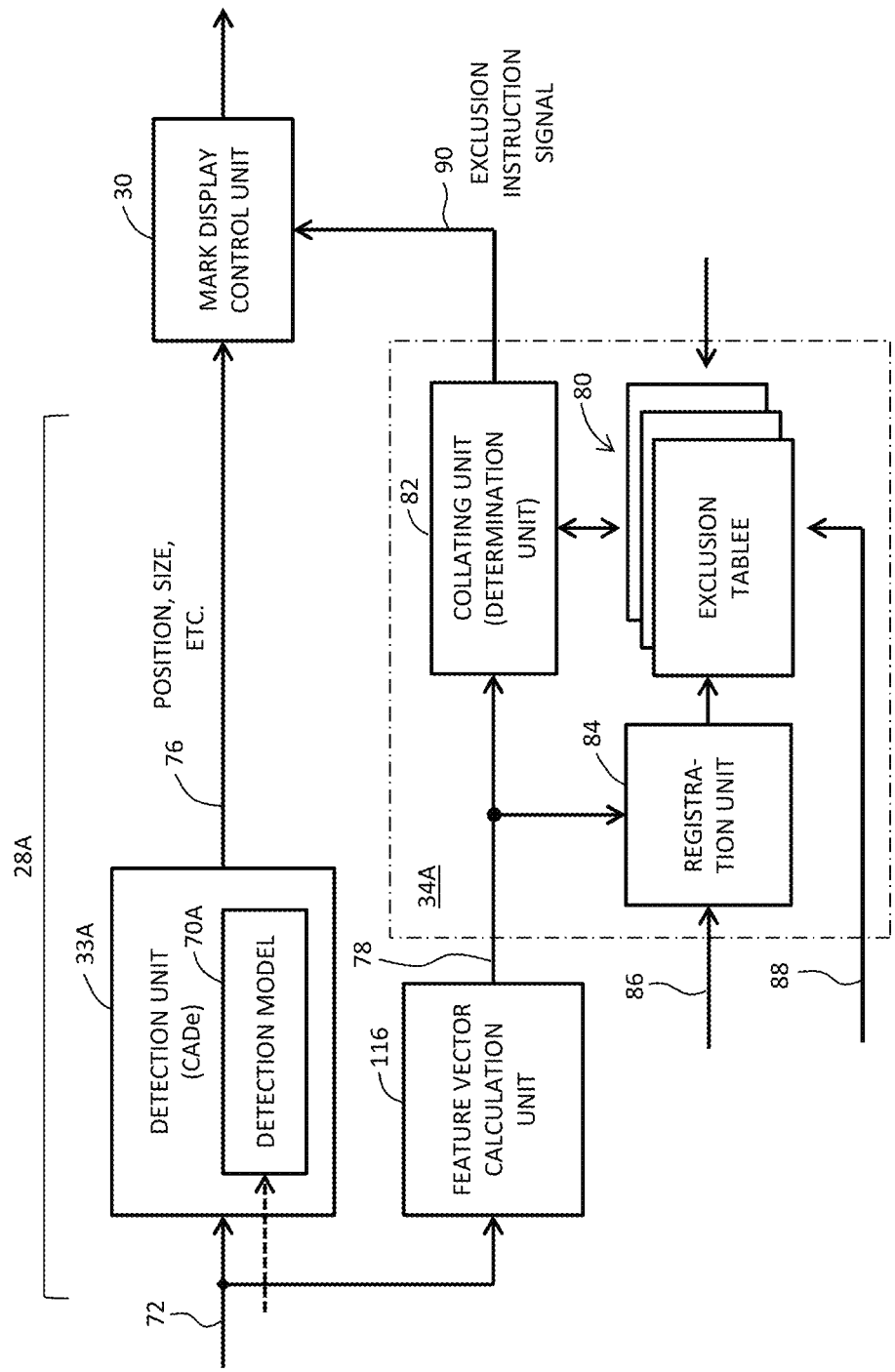
FIG. 8 illustrates a second exemplary structure of an image analyzing unit.

FIG. 8 illustrates a second exemplary structure of an image analyzing unit. In FIG. 8, structural components similar to those illustrated in FIG. 3 are assigned the same or corresponding reference numerals, and are not described again.

An image analyzing unit 28A includes a detection unit 33A and an exclusion processing unit 34A, and further a feature vector calculation unit 116. The feature vector calculation unit 116 is provided separately from the detection unit 33A, and calculates a feature vector of a lesion candidate. The feature vector calculation unit 116 is not a machine learning calculation unit, but a general calculation unit. The detection unit 33A has a machine learned detection model 70A, but does not have a function of calculating a feature vector. In the second exemplary structure as well, the exclusion processing unit 34A executes an exclusion processing, using the exclusion database 80. A management unit is not illustrated in FIG. 8.

Figure 9:
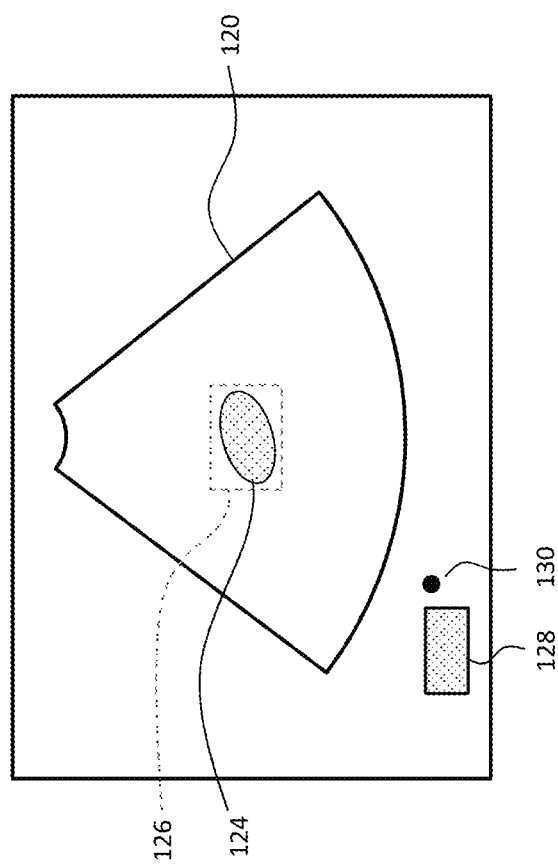
FIG. 9 illustrates a modified example.

FIG. 9 illustrates a modified example of the display of the image. In the real time operation state, a tomographic image 120 as a motion image is displayed. The displayed tomographic image 120 contains a lesion candidate, or a detection target, with a mark 126 not displayed. In this case, an indicator 128 for indicating that the exclusion processing mode is valid may be displayed. Alternatively, an indicator 130 for indicating that displaying a mark is restricted may be displayed.

According to the above-described embodiment, a lesion candidate to be marked can be flexibly customized without relearning by a machine learning detection unit. An additional database may be provided together with, or in place of, the exclusion database.

The invention claimed is:

1. An ultrasonic diagnostic device, comprising:
a detector having a machine learned detection model, the detector being configured to detect, using the machine learned detection model, a lesion candidate in an ultrasonic image;
a database configured to contain features of lesion candidates to be excluded;
a determiner configured to determine whether the detected lesion candidate is an exclusion target, by collating a feature of the detected lesion candidate with the features registered in the database; and
a controller configured to display a mark for indicating the detected lesion candidate on the ultrasonic image in a case where the detected lesion candidate is not an exclusion target, the controller being configured to restrict display of the mark in a case where the determiner determines that the detected lesion candidate is an exclusion target;
an inputter configured to receive an exclusion instruction while the lesion candidate and the mark are displayed on the ultrasonic image; and
a register configured to register, in the database, a feature of a lesion candidate addressed by the exclusion instruction, wherein
the detector has a function of obtaining the feature of the lesion candidate, and the registered feature of the lesion candidate addressed by the exclusion instruction is the feature obtained by the detector, and
lesion candidates to be marked are correctable by the exclusion instruction without relearning of the machine learned detection model.

2. The ultrasonic diagnostic device according to claim 1, wherein the inputter receives the exclusion instruction in a frozen state, and the register registers the feature of the lesion candidate addressed by the exclusion instruction in the database in the frozen state to thereby update the database.

3. The ultrasonic diagnostic device according to claim 1, wherein the inputter receives the exclusion instruction in a realtime operation state, and the register specifies one or more sets of frame data displayed, based on a time of reception of the exclusion instruction, in the real time operation state, and extracts a feature of a lesion candidate from the one or more sets of specified frame data to register the feature in the database in the real time operation state to thereby update the database.

4. The ultrasonic diagnostic device according to claim 1, further comprising
a calculator provided separately from the detector, the calculator being configured to calculate the feature of the lesion candidate.

5. The ultrasonic diagnostic device according to claim 1, further comprising
a manager configured to clear entirety or a part of the database.

6. The ultrasonic diagnostic device according to claim 5, wherein
the database includes a plurality of tables,
each of the tables has at least one feature registered therein, and
the manager selects a table to clear from among the plurality of tables.

7. A diagnostic assisting method by an ultrasonic diagnostic device, the diagnostic assisting method comprising the steps of:
(a) detecting, by the ultrasonic diagnostic device employing a machine learned detection model, a lesion candidate in an ultrasonic image;
(b) registering, in a database, features of lesion candidates to be excluded;
(c) determining, by the ultrasonic diagnostic device, whether the detected lesion candidate is an exclusion target, by collating a feature of the detected lesion candidate with the features registered in the database in (b);
(d) displaying a mark for indicating the detected lesion candidate on the ultrasonic image in a case where the detected lesion candidate is not an exclusion target, and restricting, by the ultrasonic diagnostic device, display of the mark in a case where the detected lesion candidate is determined by the ultrasonic diagnostic device to be an exclusion target;
(e) receiving, by the ultrasonic diagnostic device, an exclusion instruction while the lesion candidate and the mark are displayed on the ultrasonic image;
(f) obtaining, by the ultrasonic diagnostic device, the feature of the lesion candidate; and
(g) registering, in the database, a feature of a lesion candidate addressed by the exclusion instruction, the registered feature of the lesion candidate addressed by the exclusion instruction being the feature obtained in (f),
lesion candidates to be marked being correctable by the exclusion instruction without relearning of the machine learned detection model.

8. A non-transitory storage medium storing a program for causing an information processing device to execute a diagnostic assisting method, the program for causing the information processing device to implement functions of:
(a) detecting, by the information processing device employing a machine learned detection model, a lesion candidate in an ultrasonic image;
(b) registering, in a database, features of lesion candidates to be excluded;
(c) determining, by the ultrasonic diagnostic device, whether the detected lesion candidate is an exclusion target, by collating a feature of the detected lesion candidate with the features registered in the database;
(d) displaying a mark for indicating the detected lesion candidate on the ultrasonic image in a case that the detected lesion candidate is not an exclusion target, and restricting, by the information processing device, display of the mark in a case where the detected lesion candidate is determined by the information processing device to be an exclusion target;
(e) receiving, by the information processing device, an exclusion instruction while the lesion candidate and the mark are displayed on the ultrasonic image;
(f) obtaining, by the information processing device, the feature of the lesion candidate; and
(g) registering, in the database, a feature of a lesion candidate addressed by the exclusion instruction, the registered feature of the lesion candidate addressed by the exclusion instruction being the feature obtained in (f),
lesion candidates to be marked being correctable by the exclusion instruction without relearning of the machine learned detection model.

* * * * *